(12) United States Patent
Lattemann et al.

(10) Patent No.: US 11,965,199 B2
(45) Date of Patent: *Apr. 23, 2024

(54) 21-HYDROXYLATION OF STEROIDS

(71) Applicant: EUROAPI, Paris (FR)

(72) Inventors: Claus Lattemann, Frankfurt am Main (DE); Thomas Stillger, Frankfurt am Main (DE); Bernd Janocha, Frankfurt am Main (DE); Hans-Falk Rasser, Frankfurt am Main (DE); Sebastian Rissom, Frankfurt am Main (DE); Simone Anderko, Saarbrücken (DE); Rita Bernhardt, Saarbrücken (DE); Frank Hannemann, Saarbrücken (DE)

(73) Assignee: SANOFI, Paris (FR)

( * ) Notice: Subject to any disclaimer, the term of this patent is extended or adjusted under 35 U.S.C. 154(b) by 19 days.

This patent is subject to a terminal disclaimer.

(21) Appl. No.: 17/589,667

(22) Filed: Jan. 31, 2022

(65) Prior Publication Data

US 2022/0228189 A1 Jul. 21, 2022

Related U.S. Application Data

(60) Continuation of application No. 16/453,651, filed on Jun. 26, 2019, now Pat. No. 11,608,514, which is a division of application No. 15/523,107, filed as application No. PCT/EP2015/075096 on Oct. 29, 2015, now Pat. No. 10,385,376.

(30) Foreign Application Priority Data

Oct. 30, 2014 (EP) .................................... 14306740

(51) Int. Cl.
*C12P 33/06* (2006.01)

(52) U.S. Cl.
CPC .................................... *C12P 33/06* (2013.01)

(58) Field of Classification Search
None
See application file for complete search history.

(56) References Cited

FOREIGN PATENT DOCUMENTS

KR 2005028279 A 3/2005

OTHER PUBLICATIONS

Ahn et al: "High-level expression of human cytochrome P450 1A2 by co-expression with human molecular chaperone HDJ-1(Hsp40)", Protein Expression and Purification, vol. 36, 2004, pp. 48-52, Elsevier.
Altschul et al: "Basic Local Alignment Search Tool." J. Mol. Biol. 1990 215: 403-410, Elsevier.
Altschul et al: "Gapped BLAST and PSI-BLAST: a new generation of protein database search programs." Nucleic Acids Res. 1997 25: 3389-3402, Oxford University Press.

(Continued)

*Primary Examiner* — David W Berke-Schlessel
(74) *Attorney, Agent, or Firm* — McDonnell Boehnen Hulbert & Berghoff LLP

(57) ABSTRACT

Generally, the present invention relates to the field of steroid hydroxylation. More specifically, the present invention relates to a method for the 21-hydroxylation of steroids in cells. It also relates to cells expressing a steroid 21-hydroxylating enzyme or steroid 21-hydroxylase, expression vectors comprising a nucleic acid encoding for a steroid 21-hydroxylase and a kit for carrying out the method for the 21-hydroxylation of steroids in cells.

20 Claims, 11 Drawing Sheets

Specification includes a Sequence Listing.

(56) References Cited

OTHER PUBLICATIONS

Brixius-Anderko et al: "A CYP21A2 based whole-cell system in Escherichia coli for the biotechnological production of premedrol", Microbial Cell Factories, vol. 14, Sep. 15, 2015 (Sep. 15, 2015), pp. 1-14, BioMed Central.

Calin-Aurel Dragan: "Expression of human steroid hydroxylases in fission yeast", Dissertation, University of Saarbrucken, 2010, Saarbrücken, Germany, pages i-xiv-1-100, XP002751430, Retrieved from the Internet <URL: http://scidok.sulb.uni-saarland.de/volltexte/2010/3485/pdf/phd_cummulative_dragan_upload.pdf>.

Ewen et al: "Adrenodoxin—a versatile ferredoxin", IUBMB Life, vol. 64, 2012, pp. 506-512, Wiley.

Gupta et al: "Co-expression of chaperonin GroEL/GroES enhances in vivo folding of yeast mitochondrial aconitase and alters the growth characteristics of *Escherichia coli*", The International Journal of Biochemistry & Cell Biology, vol. 38, 2006, pp. 1975-1985, Elsevier.

Hannemann et al: "design of an *Escherichia coli* system for whole cell mediated steroid synthesis and molecular evaluation of steroid hydroxylases", Journal of Biotechnology, vol. 124, 2006, pp. 172-181, Elsevier.

International Preliminary Report on Patentability, dated May 2, 2017, European Patent Office, issued in international patent application No. PCT/EP2015/075096.

International Search Report and Written Opinion, dated May 6, 2016, European Patent Office, issued in international patent application No. PCT/EP2015/075096.

Janocha et al: "Design and characterization of an efficient CYP105A1-based whole-cell biocatalyst for the conversion of resin acid diterpenoids in permeabilized *Escherichia coli*", Applied Microbiology and Biotechnology, vol. 97, Jun. 23, 2013 (Jun. 23, 2013), pp. 7639-7649, Springer.

Kang et al: "Coexpression of molecular chaperone enhances activity and export of organophosphorus hydrolase in *Escherichia coli*", Biotechnology Progress, vol. 15, 2012, pp. 925-930, Wiley.

Karlin and Altschul: "Applications and statistics for multiple high-scoring segments in molecular sequences." Proc. Natl. Acad. Sci. USA 1993 90:5873-5877, National Academies Press.

Lah et al: "The versatility of the fungal cytochrome P450 monooxygenase system is instrumental in xenobiotic detoxification", Molecular Microbiology, vol. 81, 2011, pp. 1374-1389, Wiley-Blackwell.

Ringle et al: "Application of a new versatile electron transfer system for cytochrome P450-based *Escherichia coli* whole-cell bioconversions", Applied Microbiology and Biotechnology, vol. 97, Dec. 20, 2012 (Dec. 20, 2012), pp. 7741-7754, Springer.

Sushko et al: "Mechanism of intermolecular interactions of microsomal cytochrome P450s CYP17 and CYP21 involved in steroid hormone biosynthesis", Biochemistry (Moscow), vol. 77, 2012, pp. 585-592, Springer.

Urlacher et al: "Cytochrome P450 monooxygenases: an update on perspectives for synthetic application", Trends in Biotechnology, vol. 30, 2012, pp. 26-36, Elsevier.

Yoshimoto et al: "Minor activities and transition state properties of the human steroid hydroxylases cytochromes P450c17 and P450c21, from reactions observed with deuterium-labeled substrates", Biochemistry, vol. 51, 2012, pp. 7064-7077, American Chemical Society.

Zehentgruber et al: "Challenges of steroid biotransformation with human cytochrome P450 monooxygenase CYP21 using resting cells of recombinant Schizosaccharomyces pompe", Journal of Biotechnology, vol. 146, 2010, pp. 179-185, Elsevier.

Auchus et al, "The enantiomer of progesterone (ent-progesterone) is a competitive inhibitor of human cytochromes P450c17 and P450c21" Arch Biochem Biophys, 2003, vol. 409, pp. 134-144.

Pechurskaya et al, "Adrenodoxin supports reactions catalyzed by microsomal steroidogenic cytochrome P450s" Biochem. Biophys. Res. Commun, 2007, vol. 353, pp. 598-604.

Arase, Miharu; et al. "Purification and characterization of bovine steroid 21-hydroxylase (P450c21) efficiently expressed in *Escherichia coli*" Biochemical and Biophysical Research Communication, 344, 400-405, 2006 (Year: 2006).

Ahn, Taeho and Yun Chui-Ho "High-Level Expression of Human Cytochrome P450 3A4 by Co-Expression with Human Molecular Chaperone HDJ-1 (Hsp40) "Archives of Pharmacal Research, 27, 319-323, 2004 (Year: 2004).

Liu, Jiaxin et al. "Combined chemical and biotechnological production of20[30H-NorDHCMT, a long-term metabolite of Oral-Turinabol (DHCMT)" Journal of Inorganic Biochemistry, 183, 165-171, 2018 (Year: 2018).

Bleicken, Caroline et al. "Functional Characterization of Three CYP21A2 Sequence Variants (p.A265V, p.W302S, p.D322G) Employing a Yeast Co-Expression System" Human Mutation, 1044, E443-E450, 2008 (Year: 2008).

Harnastai et al. "The Development of an Efficient System for Heterologous Expression of Cytochrom P450s in *Escherichia coli* using hem A Gene Co-Expression" Portein Expr Purif. (2006) vol. 46(1), pp. 47-55.

Wildtype human amino acid sequence:

*MLLLGLLLLLPLLAGARLLWNWWKLRSLHL*PPLAPGFLHLLQPDLPIYLLGLTQKFGPIYRLHL
GLQDVVVLNSKRTIEEAMVKKWADFAGRPEPLTYKLVSRNYPDLSLGDYSLLWKAHKKLTR
SALLLGIRDSMEPVVEQLTQEFCERMRAQPGTPVAIEEEFSLLTCSIICYLTFGDKIKDDNLM
PAYYKCIQEVLKTWSHWSIQIVDVIPFLRFFPNPGLRRLKQAIEKRDHIVEMQLRQHKESLVA
GQWRDMMDYMLQGVAQPSMEEGSGQLLEGHVHMAAVDLLIGGTETTANTLSWAVVFLLH
HPEIQQRLQEELDHELGPGASSSRVPYKDRARLPLLNATIAEVLRLRPVVPLALPHRTTRPS
SISGYDIPEGTVIIPNLQGAHLDETVWERPHEFWPDRFLEPGKNSRALAFGCGARVCLGEPL
ARLELFVVLTRLLQAFTLLPSGDALPSLQPLPHCSVILKMQPFQVRLQPRGMGAHSPGQSQ

Modified human amino acid sequence:

MAKKTSSKGKPPLAPGFLHLLQPDLPIYLLGLTQKFGPIYRLHLGLQDVVVLNSKRTIEEAMV
KKWADFAGRPEPLTYKLVSRNYPDLSLGDYSLLWKAHKKLTRSALLLGIRDSMEPVVEQLT
QEFCERMRAQPGTPVAIEEEFSLLTCSIICYLTFGDKIKDDNLMPAYYKCIQEVLKT WSHWSI
QIVDVIPFLRFFPNPGLRRLKQAIEKRDHIVEMQLRQHKESLVAGQWR DMMDYMLQGVAQP
SMEEGSGQLLEGHVHMAAVDLLIGGTETTANTLSWAVVFLLHHPEIQQRLQEELDHELGPG
ASSSRVPYKDRARLPLLNATIAEVLRLRPVVPLALPHRTTRPSSISGYDIPEGTVIIPNLQGAH
LDETVWERPHEFWPDRFLEPGKNSRALAFGCGARVCLGEPLARLELFVVLTRLLQAFTLLP
SGDALPSLQPLPHCSVILKMQPFQVRLQPRGMGAHSPGQSQHHHHHH

Wildtype bovine amino acid sequence:

*MVLAGLLLLLTLLAGAHLLWGRWKLRNLHL*PPLVPGFLHLLQPNLPIHLLSLTQKLGPVYRLR
LGLQEVVVLNSKRTIEEAMIRKWVDFAGRPQIPSYKLVSQRCQDISLGDYSLLWKAHKKLTR
SALLLGTRSSMEPWVDQLTQEFCERMRVQAGAPVTIQKEFSLLTCSIICYLTFGNKEDTLVH
AFHDCVQDLMKTWDHWSIQILDMVPFLRFFPNPGLWRLKQAIENRDHMVEKQLTRHKESM
VAGQWRDMTDYMLQGVGRQRVEEGPGQLLEGHVHMSVVDLFIGGTETTASTLSWAVAFL
LHHPEIQRRLQEELDRELGPGASCSRVTYKDRARLPLLNATIAEVLRLRPVVPLALPHRTTRP
SSIFGYDIPEGMVVIPNLQGAHLDETVWEQPHEFRPDRFLEPGANPSALAFGCGARVCLGE
SLARLELFVVLLRLLQAFTLLPPPVGALPSLQPDPYCGVNLKVQPFQVRLQPRGVEAGAWE
SASAQ

Modified bovine amino acid sequence:

MAKKTSSKGKPPLVPGFLHLLQPNLPIHLLSLTQKLGPVYRLRLGLQEVVVLNSKRTIEEAMI
RKWVDFAGRPQIPSYKLVSQRCQDISLGDYSLLWKAHKKLTRSALLLGTRSSMEPWVDQLT
QEFCERMRVQAGAPVTIQKEFSLLTCSIICYLTFGNKEDTLV HAFHDCVQDLMKTWDHWSIQ
ILDMVPFLRFFPNPGLWRLKQAIENRDHMVEKQLTRHKESMVAGQWRDMTDYMLQGVGR
QRVEEGPGQLLEGHVHMSVVDLFIGGTETTASTLSWAVAFLLHHPEIQRRLQEELDRELGP
GASCSRVTYKDRARLPLLNATIAEVLRLRPVVPLALPHRTTRPSSIFGYDIPEGMVVIPNLQG
AHLDETVWEQPHEFRPDRFLEPGANPSALAFGCGARVCLGESLARLELFVVLLRLLQAFTLL
PPPVGALPSLQPDPYCGVNLKVQPFQVRLQPRGVEAGAWESASAQHHHHHH

SEQUENCE LISTING

```
<160> NUMBER OF SEQ ID NOS: 4

<210> SEQ ID NO 1
<211> LENGTH: 495
<212> TYPE: PRT
<213> ORGANISM: Homo sapiens

<400> SEQUENCE: 1

Met Leu Leu Leu Gly Leu Leu Leu Leu Pro Leu Leu Ala Gly Ala
1               5                   10                  15

Arg Leu Leu Trp Asn Trp Trp Lys Leu Arg Ser Leu His Leu Pro Pro
                20                  25                  30

Leu Ala Pro Gly Phe Leu His Leu Leu Gln Pro Asp Leu Pro Ile Tyr
            35                  40                  45

Leu Leu Gly Leu Thr Gln Lys Phe Gly Pro Ile Tyr Arg Leu His Leu
    50                  55                  60

Gly Leu Gln Asp Val Val Val Leu Asn Ser Lys Arg Thr Ile Glu Glu
65                  70                  75                  80

Ala Met Val Lys Lys Trp Ala Asp Phe Ala Gly Arg Pro Glu Pro Leu
                85                  90                  95

Thr Tyr Lys Leu Val Ser Arg Asn Tyr Pro Asp Leu Ser Leu Gly Asp
            100                 105                 110

Tyr Ser Leu Leu Trp Lys Ala His Lys Lys Leu Thr Arg Ser Ala Leu
        115                 120                 125

Leu Leu Gly Ile Arg Asp Ser Met Glu Pro Val Val Glu Gln Leu Thr
    130                 135                 140
```

Gln Glu Phe Cys Glu Arg Met Arg Ala Gln Pro Gly Thr Pro Val Ala
145                 150                 155                 160

Ile Glu Glu Phe Ser Leu Leu Thr Cys Ser Ile Ile Cys Tyr Leu
            165                 170                 175

Thr Phe Gly Asp Lys Ile Lys Asp Asp Asn Leu Met Pro Ala Tyr Tyr
            180                 185                 190

Lys Cys Ile Gln Glu Val Leu Lys Thr Trp Ser His Trp Ser Ile Gln
            195                 200                 205

Ile Val Asp Val Ile Pro Phe Leu Arg Phe Phe Pro Asn Pro Gly Leu
210                 215                 220

Arg Arg Leu Lys Gln Ala Ile Glu Lys Arg Asp His Ile Val Glu Met
225                 230                 235                 240

Gln Leu Arg Gln His Lys Glu Ser Leu Val Ala Gly Gln Trp Arg Asp
            245                 250                 255

Met Met Asp Tyr Met Leu Gln Gly Val Ala Gln Pro Ser Met Glu Glu
            260                 265                 270

Gly Ser Gly Gln Leu Leu Glu Gly His Val His Met Ala Ala Val Asp
            275                 280                 285

Leu Leu Ile Gly Gly Thr Glu Thr Thr Ala Asn Thr Leu Ser Trp Ala
            290                 295                 300

Val Val Phe Leu Leu His His Pro Glu Ile Gln Gln Arg Leu Gln Glu
305                 310                 315                 320

Glu Leu Asp His Glu Leu Gly Pro Gly Ala Ser Ser Arg Val Pro
            325                 330                 335

Tyr Lys Asp Arg Ala Arg Leu Pro Leu Leu Asn Ala Thr Ile Ala Glu
            340                 345                 350

Val Leu Arg Leu Arg Pro Val Val Pro Leu Ala Leu Pro His Arg Thr
            355                 360                 365

Thr Arg Pro Ser Ser Ile Ser Gly Tyr Asp Ile Pro Glu Gly Thr Val
            370                 375                 380

Ile Ile Pro Asn Leu Gln Gly Ala His Leu Asp Glu Thr Val Trp Glu
385                 390                 395                 400

Arg Pro His Glu Phe Trp Pro Asp Arg Phe Leu Glu Pro Gly Lys Asn
                405                 410                 415

Ser Arg Ala Leu Ala Phe Gly Cys Gly Ala Arg Val Cys Leu Gly Glu
            420                 425                 430

Pro Leu Ala Arg Leu Glu Leu Phe Val Val Leu Thr Arg Leu Leu Gln
            435                 440                 445

Ala Phe Thr Leu Leu Pro Ser Gly Asp Ala Leu Pro Ser Leu Gln Pro
            450                 455                 460

Leu Pro His Cys Ser Val Ile Leu Lys Met Gln Pro Phe Gln Val Arg
465                 470                 475                 480

Leu Gln Pro Arg Gly Met Gly Ala His Ser Pro Gly Gln Ser Gln
            485                 490                 495

<210> SEQ ID NO 2
<211> LENGTH: 496
<212> TYPE: PRT
<213> ORGANISM: Bos taurus

<400> SEQUENCE: 2

Met Val Leu Ala Gly Leu Leu Leu Leu Thr Leu Leu Ala Gly Ala
1               5                   10                  15

His Leu Leu Trp Gly Arg Trp Lys Leu Arg Asn Leu His Leu Pro Pro

-continued

```
                20                  25                  30
Leu Val Pro Gly Phe Leu His Leu Leu Gln Pro Asn Leu Pro Ile His
                35                  40                  45
Leu Leu Ser Leu Thr Gln Lys Leu Gly Pro Val Tyr Arg Leu Arg Leu
 50                  55                  60
Gly Leu Gln Glu Val Val Leu Asn Ser Lys Arg Thr Ile Glu Glu
 65                  70                  75                  80
Ala Met Ile Arg Lys Trp Val Asp Phe Ala Gly Arg Pro Gln Ile Pro
                85                  90                  95
Ser Tyr Lys Leu Val Ser Gln Arg Cys Gln Asp Ile Ser Leu Gly Asp
                100                 105                 110
Tyr Ser Leu Leu Trp Lys Ala His Lys Lys Leu Thr Arg Ser Ala Leu
                115                 120                 125
Leu Leu Gly Thr Arg Ser Met Glu Pro Trp Val Asp Gln Leu Thr
                130                 135                 140
Gln Glu Phe Cys Glu Arg Met Arg Val Gln Ala Gly Ala Pro Val Thr
145                 150                 155                 160
Ile Gln Lys Glu Phe Ser Leu Leu Thr Cys Ser Ile Ile Cys Tyr Leu
                165                 170                 175
Thr Phe Gly Asn Lys Glu Asp Thr Leu Val His Ala Phe His Asp Cys
                180                 185                 190
Val Gln Asp Leu Met Lys Thr Trp Asp His Trp Ser Ile Gln Ile Leu
                195                 200                 205
Asp Met Val Pro Phe Leu Arg Phe Phe Pro Asn Pro Gly Leu Trp Arg
                210                 215                 220
Leu Lys Gln Ala Ile Glu Asn Arg Asp His Met Val Glu Lys Gln Leu
225                 230                 235                 240
Thr Arg His Lys Glu Ser Met Val Ala Gly Gln Trp Arg Asp Met Thr
                245                 250                 255
Asp Tyr Met Leu Gln Gly Val Gly Arg Gln Arg Val Glu Glu Gly Pro
                260                 265                 270
Gly Gln Leu Leu Glu Gly His Val His Met Ser Val Val Asp Leu Phe
                275                 280                 285
Ile Gly Gly Thr Glu Thr Thr Ala Ser Thr Leu Ser Trp Ala Val Ala
                290                 295                 300
Phe Leu Leu His His Pro Glu Ile Gln Arg Arg Leu Gln Glu Glu Leu
305                 310                 315                 320
Asp Arg Glu Leu Gly Pro Gly Ala Ser Cys Ser Arg Val Thr Tyr Lys
                325                 330                 335
Asp Arg Ala Arg Leu Pro Leu Leu Asn Ala Thr Ile Ala Glu Val Leu
                340                 345                 350
Arg Leu Arg Pro Val Val Pro Leu Ala Leu Pro His Arg Thr Thr Arg
                355                 360                 365
Pro Ser Ser Ile Phe Gly Tyr Asp Ile Pro Glu Gly Met Val Val Ile
                370                 375                 380
Pro Asn Leu Gln Gly Ala His Leu Asp Glu Thr Val Trp Glu Gln Pro
385                 390                 395                 400
His Glu Phe Arg Pro Asp Arg Phe Leu Glu Pro Gly Ala Asn Pro Ser
                405                 410                 415
Ala Leu Ala Phe Gly Cys Gly Ala Arg Val Cys Leu Gly Glu Ser Leu
                420                 425                 430
Ala Arg Leu Glu Leu Phe Val Val Leu Arg Leu Leu Gln Ala Phe
                435                 440                 445
```

```
Thr Leu Leu Pro Pro Val Gly Ala Leu Pro Ser Leu Gln Pro Asp
    450                 455                 460

Pro Tyr Cys Gly Val Asn Leu Lys Val Gln Pro Phe Gln Val Arg Leu
465                 470                 475                 480

Gln Pro Arg Gly Val Glu Ala Gly Ala Trp Glu Ser Ala Ser Ala Gln
                485                 490                 495

<210> SEQ ID NO 3
<211> LENGTH: 481
<212> TYPE: PRT
<213> ORGANISM: Homo sapiens

<400> SEQUENCE: 3

Met Ala Lys Lys Thr Ser Ser Lys Gly Lys Pro Pro Leu Ala Pro Gly
1               5                   10                  15

Phe Leu His Leu Leu Gln Pro Asp Leu Pro Ile Tyr Leu Leu Gly Leu
                20                  25                  30

Thr Gln Lys Phe Gly Pro Ile Tyr Arg Leu His Leu Gly Leu Gln Asp
            35                  40                  45

Val Val Val Leu Asn Ser Lys Arg Thr Ile Glu Glu Ala Met Val Lys
50                  55                  60

Lys Trp Ala Asp Phe Ala Gly Arg Pro Glu Pro Leu Thr Tyr Lys Leu
65                  70                  75                  80

Val Ser Arg Asn Tyr Pro Asp Leu Ser Leu Gly Asp Tyr Ser Leu Leu
                85                  90                  95

Trp Lys Ala His Lys Lys Leu Thr Arg Ser Ala Leu Leu Leu Gly Ile
            100                 105                 110

Arg Asp Ser Met Glu Pro Val Val Glu Gln Leu Thr Gln Glu Phe Cys
            115                 120                 125

Glu Arg Met Arg Ala Gln Pro Gly Thr Pro Val Ala Ile Glu Glu Glu
130                 135                 140

Phe Ser Leu Leu Thr Cys Ser Ile Ile Cys Tyr Leu Thr Phe Gly Asp
145                 150                 155                 160

Lys Ile Lys Asp Asp Asn Leu Met Pro Ala Tyr Tyr Lys Cys Ile Gln
                165                 170                 175

Glu Val Leu Lys Thr Trp Ser His Trp Ser Ile Gln Ile Val Asp Val
            180                 185                 190

Ile Pro Phe Leu Arg Phe Phe Pro Asn Pro Gly Leu Arg Arg Leu Lys
            195                 200                 205

Gln Ala Ile Glu Lys Arg Asp His Ile Val Glu Met Gln Leu Arg Gln
210                 215                 220

His Lys Glu Ser Leu Val Ala Gly Gln Trp Arg Asp Met Met Asp Tyr
225                 230                 235                 240

Met Leu Gln Gly Val Ala Gln Pro Ser Met Glu Gly Ser Gly Gln
                245                 250                 255

Leu Leu Glu Gly His Val His Met Ala Ala Val Asp Leu Leu Ile Gly
            260                 265                 270

Gly Thr Glu Thr Thr Ala Asn Thr Leu Ser Trp Ala Val Val Phe Leu
            275                 280                 285

Leu His His Pro Glu Ile Gln Gln Arg Leu Gln Glu Glu Leu Asp His
            290                 295                 300

Glu Leu Gly Pro Gly Ala Ser Ser Ser Arg Val Pro Tyr Lys Asp Arg
305                 310                 315                 320

Ala Arg Leu Pro Leu Leu Asn Ala Thr Ile Ala Glu Val Leu Arg Leu
```

```
                         325                 330                 335
Arg Pro Val Val Pro Leu Ala Leu Pro His Arg Thr Thr Arg Pro Ser
                340                 345                 350

Ser Ile Ser Gly Tyr Asp Ile Pro Glu Gly Thr Val Ile Ile Pro Asn
            355                 360                 365

Leu Gln Gly Ala His Leu Asp Glu Thr Val Trp Glu Arg Pro His Glu
        370                 375                 380

Phe Trp Pro Asp Arg Phe Leu Glu Pro Gly Lys Asn Ser Arg Ala Leu
385                 390                 395                 400

Ala Phe Gly Cys Gly Ala Arg Val Cys Leu Gly Glu Pro Leu Ala Arg
                405                 410                 415

Leu Glu Leu Phe Val Val Leu Thr Arg Leu Leu Gln Ala Phe Thr Leu
                420                 425                 430

Leu Pro Ser Gly Asp Ala Leu Pro Ser Leu Gln Pro Leu Pro His Cys
                435                 440                 445

Ser Val Ile Leu Lys Met Gln Pro Phe Gln Val Arg Leu Gln Pro Arg
            450                 455                 460

Gly Met Gly Ala His Ser Pro Gly Gln Ser Gln His His His His His
465                 470                 475                 480

His

<210> SEQ ID NO 4
<211> LENGTH: 482
<212> TYPE: PRT
<213> ORGANISM: bos taurus

<400> SEQUENCE: 4

Met Ala Lys Lys Thr Ser Ser Lys Gly Lys Pro Pro Leu Val Pro Gly
1               5                   10                  15

Phe Leu His Leu Leu Gln Pro Asn Leu Pro Ile His Leu Leu Ser Leu
                20                  25                  30

Thr Gln Lys Leu Gly Pro Val Tyr Arg Leu Arg Leu Gly Leu Gln Glu
            35                  40                  45

Val Val Val Leu Asn Ser Lys Arg Thr Ile Glu Glu Ala Met Ile Arg
50                  55                  60

Lys Trp Val Asp Phe Ala Gly Arg Pro Gln Ile Pro Ser Tyr Lys Leu
65                  70                  75                  80

Val Ser Gln Arg Cys Gln Asp Ile Ser Leu Gly Asp Tyr Ser Leu Leu
                85                  90                  95

Trp Lys Ala His Lys Lys Leu Thr Arg Ser Ala Leu Leu Leu Gly Thr
            100                 105                 110

Arg Ser Ser Met Glu Pro Trp Val Asp Gln Leu Thr Gln Glu Phe Cys
        115                 120                 125

Glu Arg Met Arg Val Gln Ala Gly Ala Pro Val Thr Ile Gln Lys Glu
    130                 135                 140

Phe Ser Leu Leu Thr Cys Ser Ile Ile Cys Tyr Leu Thr Phe Gly Asn
145                 150                 155                 160

Lys Glu Asp Thr Leu Val His Ala Phe His Asp Cys Val Gln Asp Leu
                165                 170                 175

Met Lys Thr Trp Asp His Trp Ser Ile Gln Ile Leu Asp Met Val Pro
            180                 185                 190

Phe Leu Arg Phe Phe Pro Asn Pro Gly Leu Trp Arg Leu Lys Gln Ala
        195                 200                 205

Ile Glu Asn Arg Asp His Met Val Glu Lys Gln Leu Thr Arg His Lys
```

```
              210                 215                 220
Glu Ser Met Val Ala Gly Gln Trp Arg Asp Met Thr Asp Tyr Met Leu
225                         230                 235                 240

Gln Gly Val Gly Arg Gln Arg Val Glu Glu Gly Pro Gly Gln Leu Leu
                    245                 250                 255

Glu Gly His Val His Met Ser Val Val Asp Leu Phe Ile Gly Gly Thr
                260                 265                 270

Glu Thr Thr Ala Ser Thr Leu Ser Trp Ala Val Ala Phe Leu Leu His
            275                 280                 285

His Pro Glu Ile Gln Arg Arg Leu Gln Glu Glu Leu Asp Arg Glu Leu
        290                 295                 300

Gly Pro Gly Ala Ser Cys Ser Arg Val Thr Tyr Lys Asp Arg Ala Arg
305                 310                 315                 320

Leu Pro Leu Leu Asn Ala Thr Ile Ala Glu Val Leu Arg Leu Arg Pro
                325                 330                 335

Val Val Pro Leu Ala Leu Pro His Arg Thr Thr Arg Pro Ser Ser Ile
                340                 345                 350

Phe Gly Tyr Asp Ile Pro Glu Gly Met Val Val Ile Pro Asn Leu Gln
            355                 360                 365

Gly Ala His Leu Asp Glu Thr Val Trp Glu Gln Pro His Glu Phe Arg
            370                 375                 380

Pro Asp Arg Phe Leu Glu Pro Gly Ala Asn Pro Ser Ala Leu Ala Phe
385                 390                 395                 400

Gly Cys Gly Ala Arg Val Cys Leu Gly Glu Ser Leu Ala Arg Leu Glu
                405                 410                 415

Leu Phe Val Val Leu Leu Arg Leu Leu Gln Ala Phe Thr Leu Leu Pro
                420                 425                 430

Pro Pro Val Gly Ala Leu Pro Ser Leu Gln Pro Asp Pro Tyr Cys Gly
            435                 440                 445

Val Asn Leu Lys Val Gln Pro Phe Gln Val Arg Leu Gln Pro Arg Gly
            450                 455                 460

Val Glu Ala Gly Ala Trp Glu Ser Ala Ser Ala Gln His His His His
465                 470                 475                 480

His His
```

21-HYDROXYLATION OF STEROIDS

This application is a continuation of U.S. application Ser. No. 16/453,651, filed Jun. 26, 2019, which is a divisional application of U.S. application Ser. No. 15/523,107, filed Apr. 28, 2017 now U.S. Pat. No. 10,385,376 issued Aug. 20, 2019, which is a national stage application under 35 U.S.C. § 371 of Intonational Application No. PCT/EP2015/075096, filed Oct. 29, 2015, which claims the benefit of European Application No. EP 14306740.3, filed Oct. 30, 2014, the disclosures of each of which are explicitly incorporated herein in their entirety by reference.

Generally, the present invention relates to the field of steroid hydroxylation. More specifically, the present invention relates to a method for the 21-hydroxylation of steroids in cells. It also relates to cells expressing a steroid 21-hydroxylating enzyme or steroid 21-hydroxylase, expression vectors comprising a nucleic acid encoding for a steroid 21-hydroxylase and a kit for carrying out the method for the 21-hydroxylation of steroids in cells.

Synthetic glucocorticoids are descendent from the natural occurring stress hormone cortisol and play a crucial role in pharmaceutical industry because of their anti-inflammatory and immune suppressive effects. Moreover, synthetic molecules often act more effective than cortisol.

Currently, the synthesis of some pharmaceutically active steroids involves a 21-hydroxylation of their precursor (see FIG. 1 for an example), which consists of a long lasting chemical multistep synthesis. By means of synthetic chemistry this hydroxylation is also difficult, as the chemical oxidants are not selective to position 21. For this reason, other functional groups have to be protected to avoid their oxidation and to direct the hydroxylation reaction towards position 21. Furthermore, the synthesis is not environmentally friendly because of the use of reagents such as iodine. Therefore, a cheap and sustainable production of pharmaceutically active steroids is highly desirable to satisfy the high demand for these important drugs.

This problem has been addressed by the present inventors by the development of whole cell biotransformation of steroids in a one-step synthesis by the enzyme CYP21A2, which is a member of the protein family of the cytochrome P450 monooxygenases and which is able to perform a highly selective hydroxylation of steroids at the 21-position of the steroid scaffold (see FIG. 2 for a scheme of the process). CYP21A2 is a mammalian membrane anchored enzyme which is located in the endoplasmic reticulum and which plays a crucial role in the steroid hormone biosynthesis. The inventors have shown that the biocatalytic system of the invention is a promising candidate to replace the established chemical synthesis. In particular, they have shown that steroids could be modified within one single hydroxylation step, leading to the one desired product, which is saving time, is environmentally friendly (no by-products were observed) and facilitates downstream processing. Furthermore and advantageously, for the steroid production in whole cells according to the invention, enzymes do not have to be purified, remain stable in the host and the addition of costly redox equivalents like NADPH is not necessary, because the cell itself serves as a donor.

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions etc.), whether supra or infra, is hereby incorporated by reference in its entirety. Nothing herein is to be construed as an admission that the invention is not entitled to antedate such disclosure by virtue of prior invention.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the word "comprise", and variations such as "comprises" and "comprising", are to be understood to imply the inclusion of a stated integer or step or group of integers or steps but not the exclusion of any other integer or step or group of integer or step. As used in this specification and the appended claims, the singular forms "a", "an", and "the" include plural referents, unless the content clearly dictates otherwise.

In a first aspect, the present invention relates to a process for the hydroxylation of the carbon atom 21 of a steroid, comprising the steps of:

a) providing a cell expressing
   (i) a heterologous CYP21A2 protein or a functional variant thereof,
   (ii) at least one heterologous electron transfer system capable of transferring electrons to CYP21A2, and
   (iii) one or more chaperones facilitating folding of CYP21A2; and b) adding the steroid to the cell.

A steroid is a type of organic compound that contains a characteristic arrangement of four cycloalkane rings that are joined to each other (shown below). The core of steroids is composed of seventeen carbon atoms bonded together that take the form of four fused rings: three cyclohexane rings (designated as rings A, B and C) and one cyclopentane ring (the D ring). The steroids vary by the functional groups attached to this four-ring core and by the oxidation state of the rings.

The hydroxylation of the carbon atom 21 of a steroid is the addition of an —OH group at position 21 as shown in the above-shown ABCD steroid ring system. The numbering of the carbon atoms is according to the IUPAC (International Union of Pure and Applied Chemistry)-approved ring lettering and atom numbering. The 21-hydroxylation of a steroid is shown in FIG. 1.

In a particular embodiment of the process of the first aspect of the invention, the steroid is a 3-keto steroid. More particularly, the steroid is a non-natural steroid, i.e. a steroid that is not produced and/or 21-hydroxylated in cells, especially human or bovine cells, which are not genetically altered.

In one embodiment, the steroid is selected from the group consisting of medrane, deltamedrane, progesterone, 17OH-progesterone, medroxyprogesterone, and 5-α-dihydro-progesterone. The 21-hydroxylation converts these particular steroids to premedrol, medrol, 11-deoxycorticosterone, 11-deoxycortisol, 21OH-medroxyprogesterone and 21OH-(5α-dihydroprogesterone), respectively. In one particular embodiment, in which the steroid is a non-natural steroid, the steroid is selected from the group consisting of medrane, deltamedrane, medroxyprogesterone, and 5-α-dihydro-progesterone.

The cell is in particular a cultured cell, cultured in any cell medium, e.g. in a growth medium, and is, in a particular embodiment, in a resting state. According to this embodiment, the cell is comprised in a buffer or medium capable of maintaining the cell rather than in a growth medium. The composition of the buffer depends on the particular cell and suitable buffers are well-known in the art. Depending on the cell-type, the cell is a suspension cell or an adherent cell. A suspension cell is a cell that may naturally live in suspension (i.e. without being attached to a surface), or a cell that has been modified to be able to survive in suspension cultures, for example to be grown to higher densities than adherent conditions would allow. An adherent cell is a cell that requires a surface, such as tissue culture plastic or microcarrier, which may be coated with extracellular matrix (such as collagen and laminin) components to increase adhesion properties and provide other signals needed for growth and differentiation. In one embodiment, the adherent cell is a monolayer cell.

Generally, the cell may be a prokaryotic cell or a eukaryotic cell. A particular example of a prokaryotic cell to be used in the process of the first aspect is an *E. coli* cell, e.g. of the *E. coli* strain C43(DE3) of the examples. A particular example of a eukaryotic cell is a yeast cell, e.g. a *S. cerevisae* cell or a *Schizosaccharomyces pombe* cell. However, the process of the first aspect is not limited to any particular cell type and any cell type may be used, in particular any cell type that can be grown and maintained in culture and that can be used as a recombinant expression system, like insect cells or mammalian cells in addition to the above-mentioned cells.

The term "heterologous" means that a protein is expressed in cell that does not normally (i.e. without human intervention) express that protein. CYP21A2, for example is an enzyme also called 21-hydroxylase, which is part of the cytochrome P450 family of enzymes. Cytochrome P450 enzymes are involved in many processes in the body, such as assisting with reactions that break down drugs and helping to produce cholesterol, certain hormones, and fats (lipids). The 21-hydroxylase enzyme is found in the adrenal glands, which are located on top of the kidneys and produce a variety of hormones that regulate many essential functions in the body. Therefore, with respect to heterologous expression, the CYP21A2 protein can be considered heterologous regarding any cell which is not an adrenal gland cell.

In particular, the term "heterologous" can also refer to the species a protein or gene is derived from in comparison to the cell in which it is expressed, in particular recombinantly expressed. A heterologous protein is then a protein that is derived from a different species than the cell it is expressed in, i.e. the cell of the process of the first aspect of the invention.

For example, the present inventors expressed mammalian, in particular human or bovine proteins in an *E. coli* cell, making these proteins heterologous with respect to the cell.

In a particular embodiment of the process of the first aspect of the invention, the CYP21A2 protein is of human or bovine origin. Human CYP21A2 (UniProt accession number P08686) has the sequence according to SEQ ID NO: 1 of the sequence listing. Bovine CYP21A2 (UniProt accession number P00191) has the sequence according to SEQ ID NO: 2 of the sequence listing. See also FIG. 8. Homologous genes, however, do also exist in other mammalian species, such as *Canis lupus* (dog), *Macaca mulata* (resus monkey), *Rattus norvegicus* (rat), *Gallus gallus* (chicken), *Danio rerio* (zebra fish), *Mus musculus* (mouse), or *Pan troglodytes* (chimpanzee). Therefore, it is emphasized that any CYP21A2 protein can be used, in particular any mammalian CYP21A2 protein. A modified human or bovine CYP21A2 according to SEQ ID NO: 3 and SEQ ID NO: 4, respectively, can also be used. See also FIG. 8. The term "functional variant" is a protein variant that has at least 20% (e.g., at least: 20%; 30%; 40%; 50%; 60%; 70%; 80%; 90%; 95%; 98%; 99%; 99.5%; or 100% or even more) of the ability of the unaltered or CYP21A2 protein to 21-hydroxylate a steroid. This ability can be determined by the skilled person without undue burden using, for example, the methods shown in Examples 1 and 2 herein.

A "protein variant" is a protein that has an amino acid sequence that it at least 70%, 80%, 85%, 90%, 95%, 96%, 97%, 98% or 99% identical to the amino acid sequence of the CYP21A2 it is derived from, for example SEQ ID NO: 1 or 3 in case of human CYP21A2 or SEQ ID NO: 2 or 4 in case of bovine CYP21A2. The determination of percent identity between two sequences is accomplished using the mathematical algorithm of Karlin and Altschul, *Proc. Natl. Acad. Sci. USA* 90, 5873-5877, 1993. Such an algorithm is incorporated into the BLASTN and BLASTP programs of Altschul et al. (1990) J. Mol. Biol. 215, 403-410. To obtain gapped alignments for comparative purposes, Gapped BLAST is utilized as described in Altschul et al. (1997) Nucleic Acids Res. 25, 3389-3402. When utilizing BLAST and Gapped BLAST programs, the default parameters of the respective programs are used.

Alternatively, a protein variant can also be defined as having up to 100, 90, 80, 70, 60, 50, 40, 30, 20, 10, 5, 4, 3, 2, or 1 amino acid substitutions, in particular conservative amino acid substitutions. Conservative subsitution tables are well known in the art (see for example Creighton (1984) Proteins. W.H. Freeman and Company). An overview of physical and chemical properties of amino acids is given in Table 1 below. In a particular embodiment, conservative substitutions are substitution made with amino acids have the same properties according to Table 1.

TABLE 1

Properties of naturally occuring proteins.

| Charge properties/ hydrophobicity | Side group | Amino Acid |
|---|---|---|
| nonpolar hydrophobic | aliphatic | Ala, Ile, Leu, Val |
| | aliphatic, S-containing | Met |
| | aromatic | Phe, Trp |
| | imino | Pro |

TABLE 1-continued

Properties of naturally occuring proteins.

| Charge properties/ hydrophobicity | Side group | Amino Acid |
|---|---|---|
| polar uncharged | aliphatic | Gly |
| | amide | Asn, Gln |
| | aromatic | Tyr |
| | hydroxyl | Ser, Thr |
| | sulfhydryl | Cys |
| positively charged | basic | Arg, His, Lys |
| negatively charged | acidic | Asp, Gly |

The term "variant" also includes protein fragments. A fragment of CYP21A2 has an N-terminal and/or C-terminal deletion of up to 100, 90, 80, 70, 60, 50, 40, 30, 20, 10, 5, 4, 3, 2, or 1 amino acids in total. In a particular embodiment, the functional variant is a fragment of CYP21A2 lacking the hydrophobic anchor region, i.e. a truncation of 29 N-terminal amino acid residues (FIG. 8).

In addition, the CYP21A2 protein may be modified, for example by N-terminal or C-terminal amino acid additions, such as tags or N-terminal modifications for improved bacterial expression. For example, the tag may be a C-terminal His-tag, e.g. 6 x His-tag and the N-terminal modification an addition of ten amino acids from the N-terminus of CYP2C3 (see FIG. 8 and SEQ ID Nos 3 and 4).

An electron transfer system is a series of compounds that transfer electrons from electron donors to electron acceptors via redox reactions. The term "capable of transferring electrons to CYP21A2" thereby means that CYP21A2 is the electron acceptor of this series. The term "series" herein may include CYP21A2 and, thus, the electron transfer system may consist of only one protein in addition to CYP21A2. For the process of the first aspect of the invention, it is not crucial which members the electron transfer system consists of, as long as the system is capable of transferring electrons to CYP21A2. Suitable systems are well-known in the art. In a particular embodiment of the process of the first aspect of the invention, the at least one electron transfer system comprises (i) a CYP21A2 reductase, or (ii) a ferredoxin reductase, preferably an NADPH-dependent ferredoxin reductase (adrenodoxin reductase) and a ferredoxin. For example, the at least one electron transfer protein can be selected from the group consisting of an NADPH-dependent cytochrome P450 reductase (CPR, e.g. human or bovine), the combination of an adrenodoxin reductase (AdR, e.g. human or bovine) and an adrenodoxin (Adx4-108, e.g. human or bovine), the combination of a flavodoxin reductase (Fpr, e.g. from E. coli) and an adrenodoxin (Adx4-108, e.g. human or bovine), the combination of an adrenodoxin reductase homolog (Arh), e.g. S. pombe adrenodoxin reductase homolog (Arh1), and an adrenodoxin (Adx4-108, e.g. human or bovine), the combination of an adrenodoxin reductase homolog (Arh), e.g. S. pombe adrenodoxin reductase homolog (Arh1), and the ferredoxin domain of an electron transfer domain (etp$^{fd}$), e.g. the ferredoxin domain of the S. pombe electron transfer domain (etp1$^{fd}$), and the combination of a flavodoxin reductase (Fpr, e.g. from E. coli) and the ferredoxin domain of an electron transfer domain (etp$^{fd}$), e.g. the ferredoxin domain of the S. pombe electron transfer domain (etp1$^{fd}$).

In a particular embodiment, exogenous NADPH is not added to the cell. In this embodiment, NADPH is produced by the cell. In a specific embodiment, the NADPH-production in the cell may be increased by recombinant means, e.g. the heterologous expression of enzymes involved in NADPH production (e.g. one or more of glucose-6-phosphate dehydrogenase (G6PD), phosphogluconate dehydrogenase (PGD), malate dehydrogenase (MDH), and/or isocitrate dehydrogenase (ICDH)), and/or it may be increased by providing hormonal signals, i.e. adding hormomes such as estradiol that enhance the level of endogenous NADPH production.

Similarly, the chaperone can be any chaperone as long as it is capable of facilitating folding of CYP21A2. The present inventors found that the process of the first aspect of the invention can rely only on endogenous chaperones, i.e. additional expression of suitable chaperones is not essential. However, an additional expression improves the production of functional CYP21A2 in the cell and can therefore be beneficial. Thus, in one embodiment of the process of the first aspect of the invention, the one or more chaperones are recombinantly expressed chaperones. In particular, the one or more chaperones may be heterologous chaperones. Exemplary chaperones are the E. coli chaperones GroEL and GroES or other chaperones like DnaK, DnaJ, GrpE, and ClpB as well as small heat shock proteins (sHSP) such as IbpA and IbpB (IbpAB).

Optionally, the same chaperone or one or more additional chaperone(s) to be expressed in the cell is/are capable of folding one or more of above electron transfer proteins.

Recombinant expression refers to the expression of a recombinant gene. Such a gene can be any gene introduced into the cell by methods of genetic engineering and is usually a heterologous gene and/or a gene regulated differently than a possible endogenous counterpart gene in terms of expression. In one embodiment, the recombinant expression is inducible.

In one embodiment of the process of the first aspect of the invention, the process further comprises adding one or more cell permeabilizing agents to the suspension of cells, for example after step b). Cell permeabilizing agents are reagents which increase the permeability of membranes. Examples are organic solvents, such as methanol, acetone or DMSO, detergents such as saponin, Triton X-100 or Tween-20, and EDTA. In particular, polymyxin B can be used as a cell permeabilizing agent. This agent proved to work particularly well in the process of the invention.

In another embodiment of the process of the first aspect of the invention, the process further comprises a step c) of extracting the 21-hydroxylated steroid from the cell and/or the supernatant of the cell (i.e. the buffer or medium the cell is comprised in), for example from a whole cell suspension. The extraction can be done with any solvents or extraction methods known in the art for extracting undissolved compounds. For example, a solvent such as 1-butanol, 2-butanone or chloroform may be used.

In a specific embodiment of the process of the first aspect of the invention, the expression of at least one tryptophanase gene is reduced or abolished in the cell. A tryptophanase or L-tryptophan indole-lyase (EC number 4.1.99.1.) is an enzyme catalyzing the reaction L-tryptophan+H2O=indole+pyruvate+NH3. Accordingly, the reduction or abolishment will lead to the decrease of indol production by the cell, which can improve the process, since indol is an inhibitor of CYP enzymes such as CYP21A2. As tryptophanase genes are generally (but not exclusively) found in prokaryotes, e.g. E. coli, this specific embodiment applies in particular to the embodiment of the process of the first aspect of the invention in which the cell is a prokaryotic cell. In one embodiment, the species of a cell expressing a tryptophansae gene is selected from the group consisting of Aeromonas hydro-

*phile, Bacillus sp., Bacteroides sp., Corynebacterium sp., Enterobacter aerogenes, Enterobacter aerogenes SM*-18, *Enterobacter sp., Erwinia sp., Escherichia aurescens, Escherichia coli, Fusobacterium necrophorum subsp. Funduliforme, Kluyvera sp., Micrococcus aerogenes, Morganella morganii, Paenibacillus alvei, Paracolobactrum coliforme, Paracolobactrum sp., Pasteurella sp., Photobacterium profundum, Porphyromonas gingivalis, Prevotella intermedia, Proteus vulgaris, Providencia rettgeri, Shigella alkalescens, Sphaerophorus sp., Symbiobacterium thermophilum, Vibrio sp.* and a mammalian species such as *Homo sapiens* and *Rattus norvegicus,*

In a further embodiment of the process of the first aspect of the invention, the cell further expresses a heterologous or recombinant gene encoding for an enzyme catalyzing a step in the heme biosynthesis pathway, in particular a heterologous hemA (glutamyl tRNA reductase) gene. An example for such cells is *E. coli*. This will advantageously reduce the need for feeding precursors for the synthesis of the CYP heme, such as the heme precursor δ-aminolevulinic acid, and reduce the costs for the biotransformation of steroids in such cells.

In a particular embodiment of the process of the first aspect of the invention, the nucleic acids encoding for (i) a heterologous CYP21A2 protein or a functional variant thereof, (ii) at least one heterologous electron transfer system capable of transferring electrons to CYP21A2, and optionally (iii) one or more chaperones facilitating folding of CYP21A2 are comprised in one or more expression cassette(s) which is/are integrated into the cell, in particular into its genome. The term "expression cassette" refers to a DNA fragment which comprises a gene operably linked to a regulatory sequence such as a promoter, necessary for gene expression. "Operably linked" refers to the linking of nucleotide regions encoding specific genetic information such that the nucleotide regions are contiguous, the functionality of the region is preserved and will perform relative to the other regions as part of a functional unit. The nucleic acids (i), (ii) and optionally (iii) may each be comprised in individual expression cassettes or in one or more multicistronic expression cassettes. As used herein, the term "multicistronic" means that multiple cistrons, namely, multiple nucleic acids or genes, are operably linked to the same regulatory sequence, e.g. a promoter.

In one embodiment, the nucleic acids encoding for (i) a heterologous CYP21A2 protein or a functional variant thereof, (ii) at least one heterologous electron transfer system capable of transferring electrons to CYP21A2, and optionally (iii) one or more chaperones facilitating folding of CYP21A2 are comprised in an expression vector comprised in the cell. An "expression vector" is a vehicle by means of which DNA fragments that contain nucleic acids encoding for a protein can be introduced into host cells where the nucleic acids can be expressed by the host cell. The nucleic acids (i), (ii) and optionally (iii) may each be comprised in individual expression vectors or in one or more multicistronic expression vectors.

Also, one or more of the nucleic acids (i), (ii) and optionally (iii) may be comprised in an expression cassette which is integrated into the cell genome, whereas the remaining nucleic acids (i), (ii) or optionally (iii) are comprised in an expression vector, both as set out above.

In a second aspect, the present invention relates to cell expressing
(i) a heterologous CYP21A2 protein or a functional variant thereof,
(ii) at least one heterologous electron transfer system capable of transferring electrons to CYP21A2, and
(iii) one or more chaperones facilitating folding of CYP21A2.

This cell as well as the cell of the process of the first aspect of the invention can also be described as a cell comprising one or more nucleic acids encoding for
(i) a heterologous CYP21A2 protein or a functional variant thereof,
(ii) at least one heterologous electron transfer system capable of transferring electrons to CYP21A2, and
(iii) one or more chaperones facilitating folding of CYP21A2.

In a particular embodiment, these nucleic acids are comprised in one or more expression cassettes.

The cell of the second aspect is in essence the cell used in the process of the first aspect of the invention and, therefore, further embodiments of the cell of the second aspect of the invention are as described above with respect to the process of the first aspect.

In a third aspect, the present invention relates to a multicistronic expression vector comprising (i) a nucleic acid encoding for a CYP21A2 protein or a functional variant thereof, (ii) one or more nucleic acids encoding for at least one heterologous electron transfer system capable of transferring electrons to CYP21A2, and optionally (iii) one or more nucleic acids encoding for chaperones facilitating folding of CYP21A2.

In a fourth aspect, the present invention relates to a kit comprising
a cell of the second aspect,
a multicistronic expression vector of the third aspect, or
(i) an expression vector comprising a nucleic acid encoding for a CYP21A2 protein or a functional variant thereof, (ii) one or more expression vectors comprising one or more nucleic acids encoding for at least one heterologous electron transfer system capable of transferring electrons to CYP21A2, and optionally (iii) one or more expression vectors comprising one or more nucleic acids encoding for chaperones facilitating folding of CYP21A2.

The term "kit" is used herein to mean a collection of all or some of the reagents, materials, and instructions necessary to carry out the process of the first aspect. This includes cell culture medium or buffer (both in dry or liquid form), one or more cell permeabilizing agents, solvents for extracting the steroid and, in particular, the steroid to be hydroxylated, in particular a 3-keto steroid, for example one or more of medrane, deltamedrane, progesterone, 17OH-progesterone, medroxyprogesterone, or 5α-dihydroprogesterone.

Furthermore, it is envisaged that all reagents or materials described herein with relation to the process of the first aspect can be part of the kit of the fourth aspect.

In a particular embodiment, the process of the first aspect, the cell of the second aspect, the expression vector of the third aspect and the kit of the fourth aspect do not comprise a further step or component as applicable, especially a heterologous gene or protein, for steroid conversion or production which is not related to the 21-hydroxylation of steroids, particularly as described herein. Optionally, an exception of this may be downstream steps or components related to the further processing of the 21-hydroxylated steroid (such as the conversion from premedrol to medrol) or upstream steps or components related to the production of the steroid to be 21-hydroxylated (such as the production of medrane).

In the following figures and examples, some particular embodiments of the invention are described in more detail. Yet, no limitation of the invention is intended by the details of the particular embodiments. In contrast, the invention pertains to any embodiment which comprises details which are not explicitly mentioned in the embodiments herein, but which the skilled person finds without undue effort.

DESCRIPTION OF THE FIGURES

FIG. 8: Amino acid sequences of wildtype and modified human (A) and bovine (B) CYP21A2.

DESCRIPTION OF THE EXAMPLES

Example 1

In vitro Hydroxylation 1.1 Expression/purification of hCYP21/bCYP21

To show that both human and bovine CYP21 are able to hydroxylate steroids at position 21, in vitro studies with both enzymes were performed. As an exemplary 21-hydroxylation process, medrane was converted to premedrol:

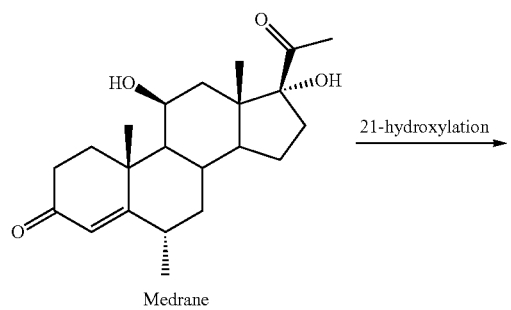

Medrane 21-hydroxylation →

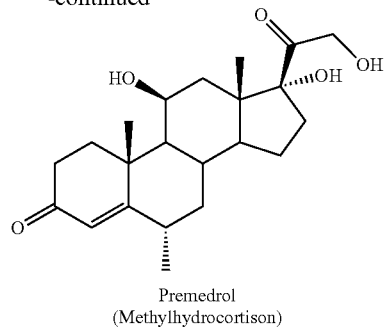

Premedrol
(Methylhydrocortison)

Premedrol (methylhydrocortisone) is a precursor of a highly effective pharmaceutical steroid medrol (methylprednisolone). Medrol is an important drug in therapy of autoimmune diseases, multiple sclerosis and in general for local and systematic treatment of inflammations.

Figure 1:
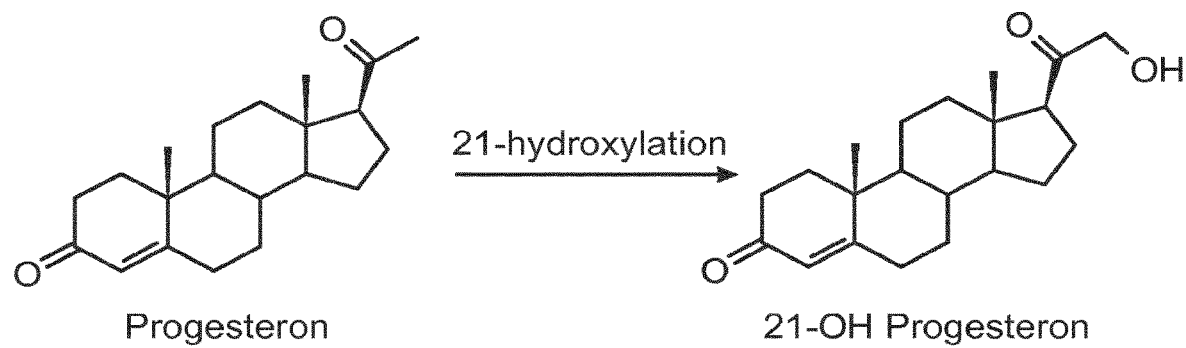
FIG. 1: Hydroxylation of a steroid (here progesterone) at carbon atom 21.
Figure 2:
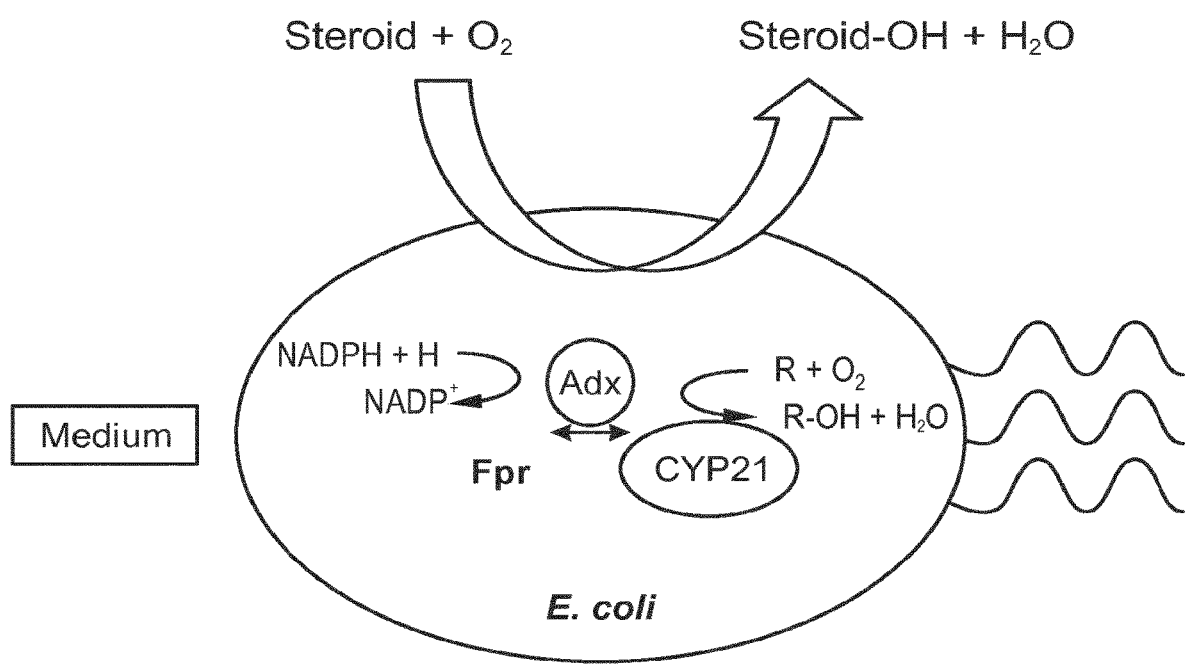
FIG. 2: Scheme of a whole cell biotransformation of a steroid by CYP21A2 and the needed electron transfer proteins in *E. coli*.
Figure 3:
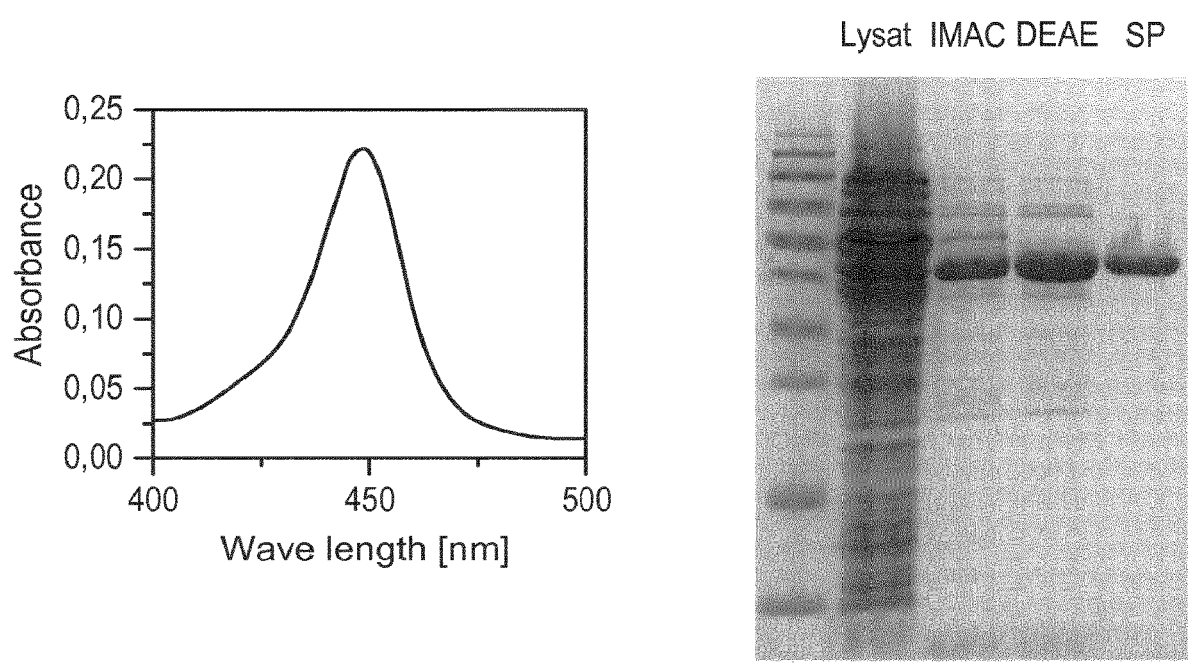
FIG. 3: left: CO difference spectrum of purified bovine CYP21; right: SDS-PAGE of bCYP21 samples taken after indicated purification steps (IMAC/DEAE/SP).

Both enzymes were expressed in the *E. coli* strain C43 (DE3) by coexpression of the *E. coli* chaperones GroEL/GroES encoded in the vector pGro12. These chaperones ensure a correct protein folding which is important for an incorporation of the heme prosthetic group. In FIG. 3 an SDS-PAGE and a CO difference spectrum of purified bovine CYP21 are shown. As the CO difference spectrum shows, the enzyme was purified in an active form. To determine the binding of medrane to both isozymes the binding constants ($K_D$-values) were determined.

1.2 Expression of Electron Delivering Redox Partners

For an efficient substrate conversion, both isoforms require an electron transfer system which consists of two parts, the cytochrome P450 enzyme itself and one or two electron transfer proteins which are essential for a hydroxylation reaction. Without these transfer proteins, no reaction will take place. Electrons can be transferred to CYP21 for example by the six electron transfer systems listed in Table 2:

TABLE 2

Electron delivering proteins applied in CYP21-dependent substrate conversions and corresponding expression plasmids for whole-cell systems. hCYP21 or bCYP21 were combined in reconstituted systems or whole-cell systems with the indicated redox partners bCPR (bovine NADPH-dependent cytochrome P450 reductase), bAdR (bovine adrenodoxin reductase), $bAdx_{4-108}$ (bovine adrenodoxin), Fpr (*E. coli* flavodoxin reductase), Arh1 (*S. pombe* adrenodoxin reductase homolog), $etp1^{fd}$ (*S. pombe* electron transfer protein, ferredoxin domain).

| Protein combinations in reconstituted in vitro systems | | Corresponding plasmids |
|---|---|---|
| Reductase | Ferredoxin | in whole-cell systems |
| 1 CPR | | p21h_bRED/p21b_bRED |
| 2 AdR | $Adx_{4-108}$ | p21h_AdAx/p21b_AdAx |
| 3 Fpr | $Adx_{4-108}$ | p21h_FrAx/p21b_FrAx |
| 4 Arh | $Adx_{4-108}$ | p21h_ArAx/p21b_ArAx |
| 5 Arh | $etp1^{fd}$ | p21h_ArET/p21b_ArET |
| 6 Fpr | $etp1^{fd}$ | p21h_FrET/p21b_FrET |

For in vitro studies and a verification of a substrate conversion, all redox partners were purified.

1.3 Reconstitution of Cytochrome P450 Systems In Vitro

Figure 4:
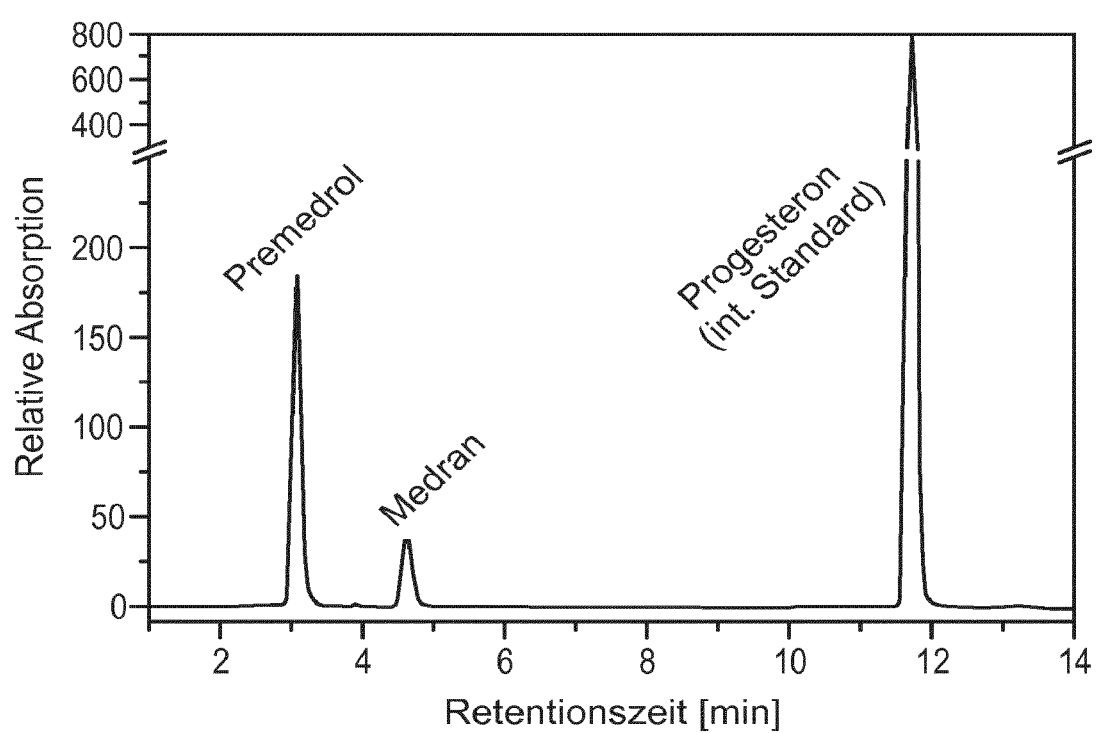
FIG. 4: HPLC chromatogram of the in vitro 21-hydroxylation of medrane to premedrol by human CYP21 and described electron transfer proteins, here AdR and Adx (system 2).

In vitro substrate conversions with purified enzymes in a defined buffer and with an NADPH regeneration system revealed that both isoforms together with the here listed electron transfer proteins are able to convert medrane to premedrol very efficiently. FIG. 4 shows the in vitro conversion of medrane by human CYP21 together with electron transfer system 2. This result indicates that steroids as exemplified by premedrol can be produced enzymatically by CYP21 together with a suitable redox system, e.g. as shown in Table 2.

Example 2

Whole-cell Systems

In view of the successful in vitro conversion of steroids, a biotransformation in whole cells was developed.

Figure 5:
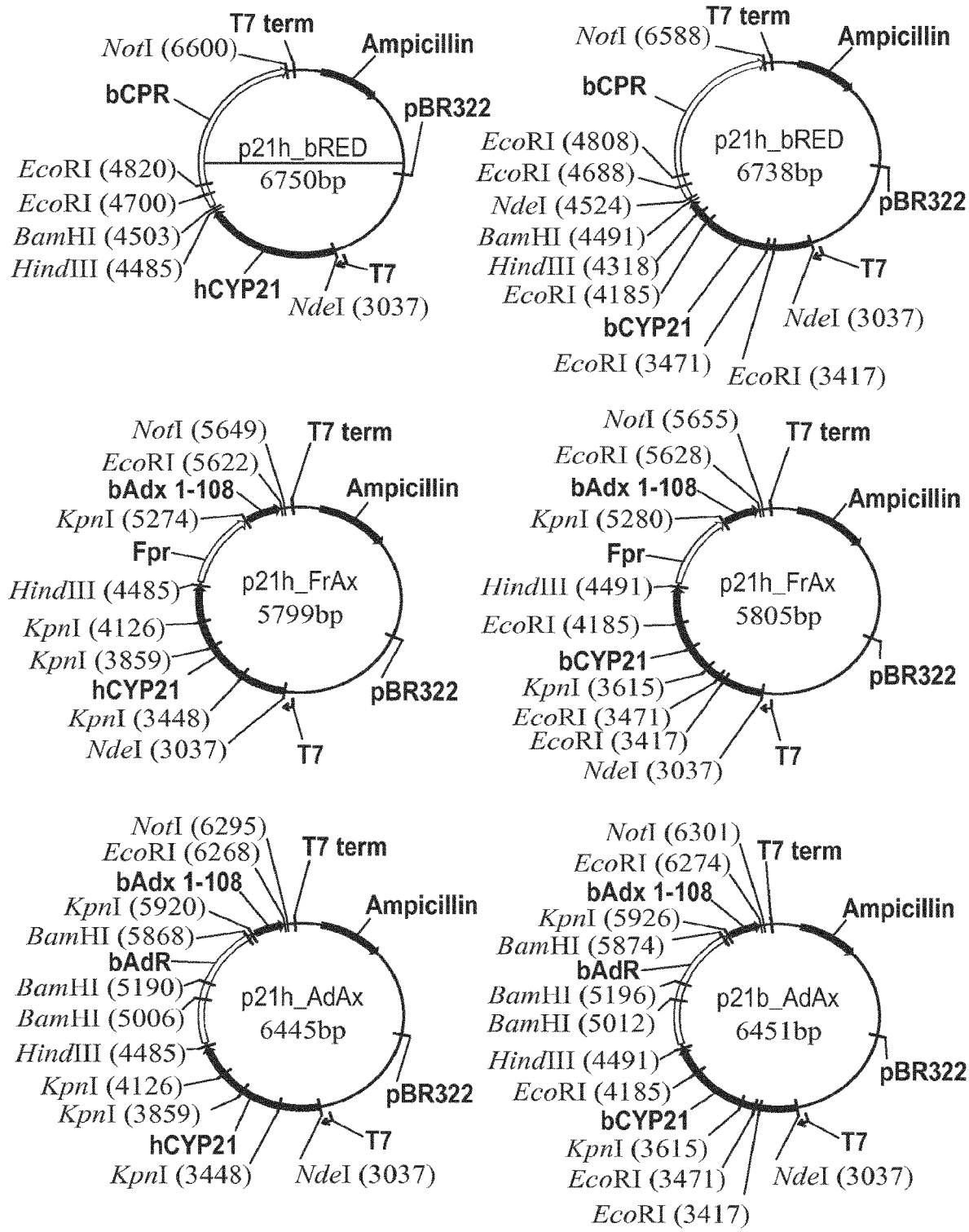
FIG. 5: Constructed vectors for whole cell biotransformation using human or bovine CYP21 with different electron transfer proteins.
Figure 5:
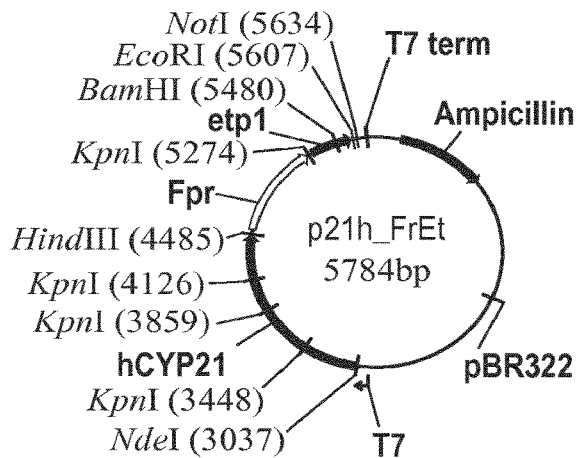
Figure 5:
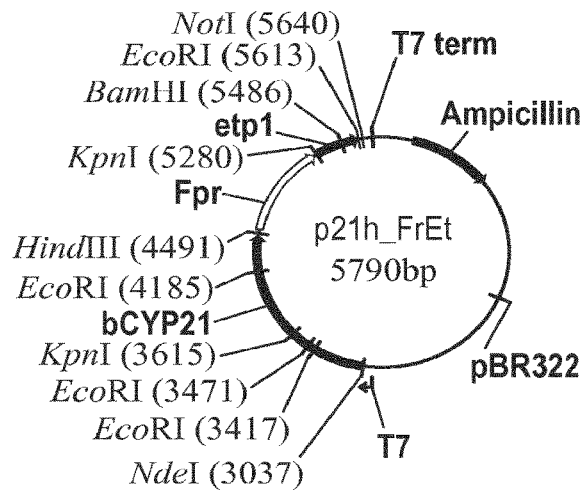
Figure 5:
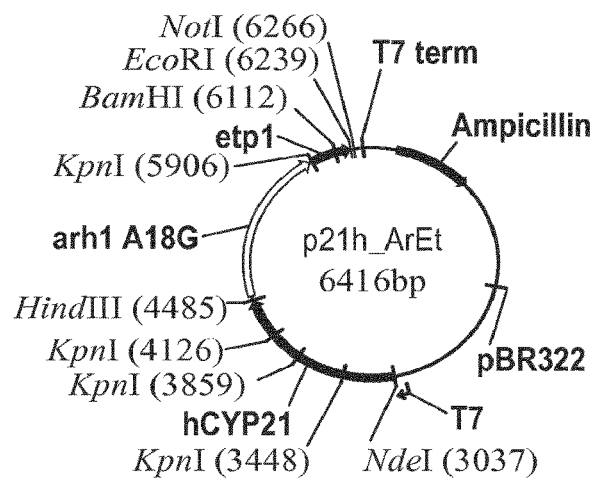
Figure 5:
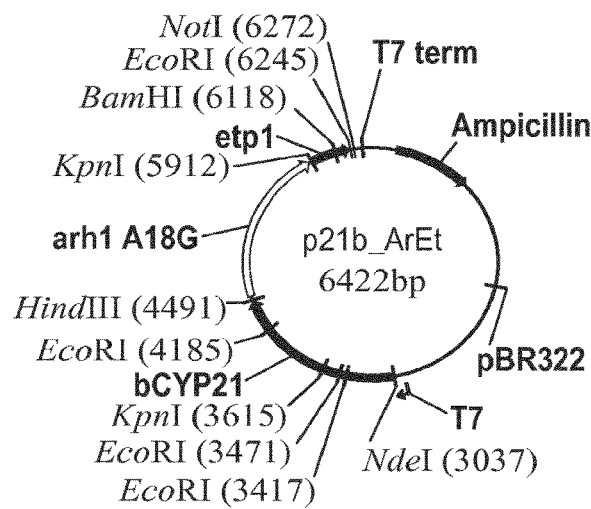
Figure 5:
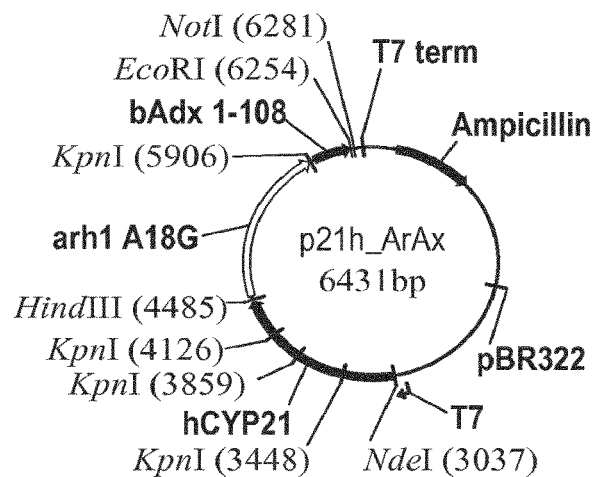
Figure 5:
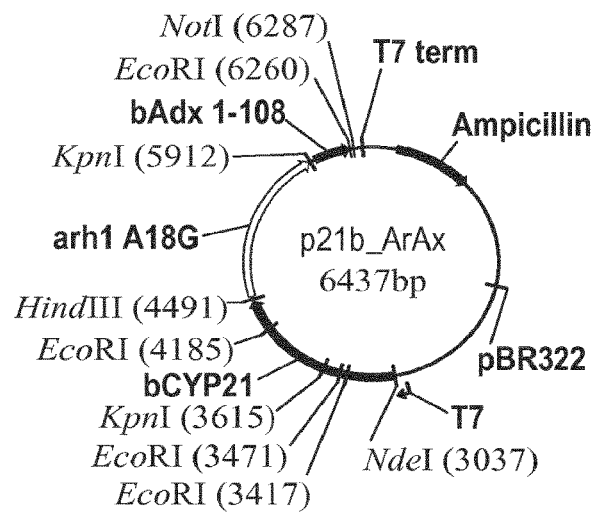

Generally, in order to perform the hydroxylation in whole cells, the CYP21 as well as the necessary electron transfer proteins were expressed heterologously in *Escherichia coli* strain C43(DE3). For expression and following conversion, bi- or tricistronic vectors based on the plasmid pET17b were constructed, which carry the genes for the particular CYP21 and the particular redox system. FIG. 5 shows all constructed vectors. To facilitate correct protein folding, the *E. coli* chaperones GroEL and GroES were co-expressed on a second vector. The transformed *E. coli* cells were able to produce the CYP21 enzyme as well as the needed redox partners. After the protein expression, a substrate conversion took place which was started by the addition of the steroid to be hydroxylated (exemplified by medrane) as a substrate.

In particular, *E. coli* strain C43(DE3) was transformed with vector for whole cell biocatalysis (e.g. p21b_ArET) and the pGro12 which encodes the chaperones GroEL/ES. The culture comprised 200 mL TB medium (+antibiotics ampicillin and kanamycin) in a 2 L Erlenmeyer flask, inoculated with 2 mL seed culture, and was grown at 37° C. Expression was induced at OD 0.5 by addition of 1 mM IPTG, 1 mM δ-aminolevulinic acid, 4 mg/mL arabinose and maintained for 28 h at 27° C. For whole cell biotransformation, cells were harvested by centrifugation and washed with 50 mM potassium phosphate buffer (pH 7.4). Substrate conversion was started with the addition of 400 μM substrate with resting cells in 25 mL potassium phosphate buffer (50 mM) including 2% glycerol, 1 mM IPTG, 1 mM δ-aminolevulinic acid, 4 mg/mL arabinose in 300 mL buffled flasks for 24 h at a cell density of ca. 24 g/L (wet weight). Samples were taken after, e.g., 24 h and measurement was performed via RP-HPLC after steroid extraction with chloroform.

Figure 6:
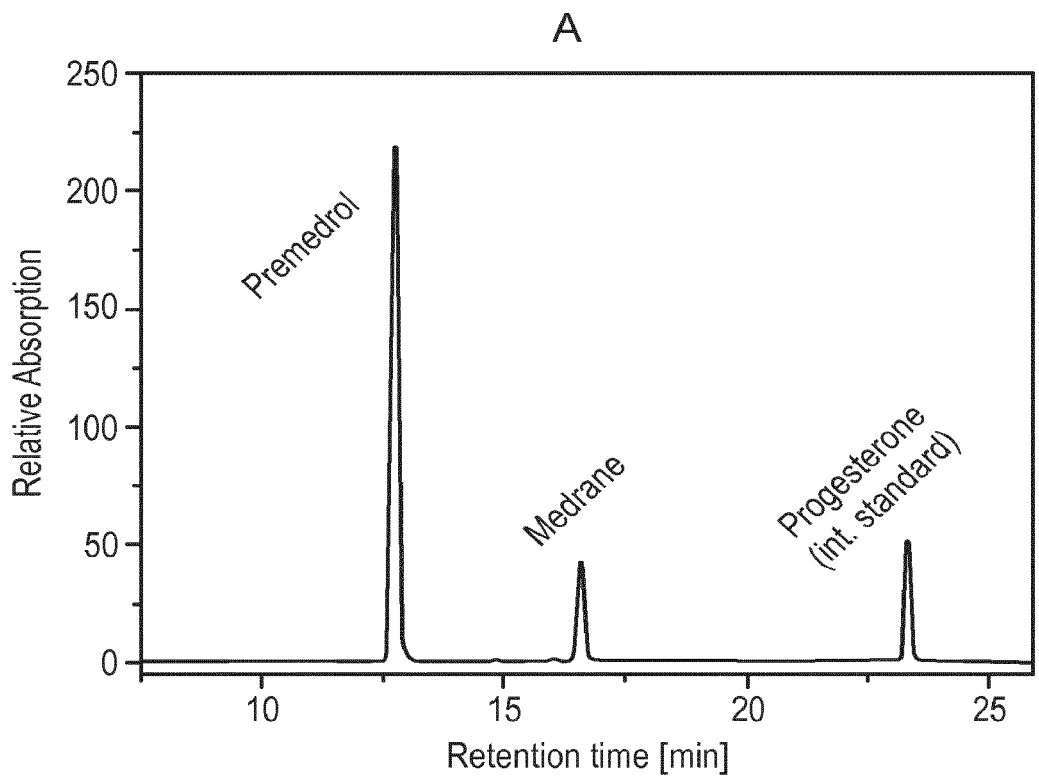
FIG. 6: HPLC chromatogram of the whole cell 21-hydroxylation of medrane to premedrol (A), delta-medrane to medrol (B), medroxyprogesterone to 21OH-medroxyprogesterone (C), and 17OH-progesterone to 11-deoxycortisol (D) by bovine CYP21 and described electron transfer proteins, here Fpr and Adx.
Figure 6:
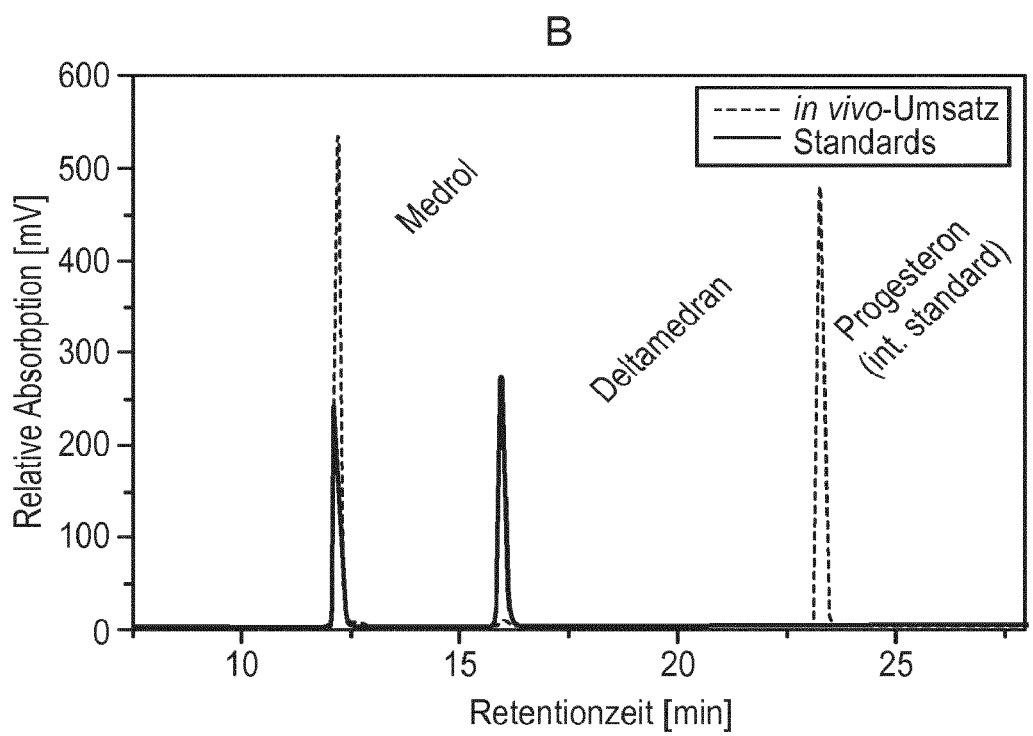
Figure 6:
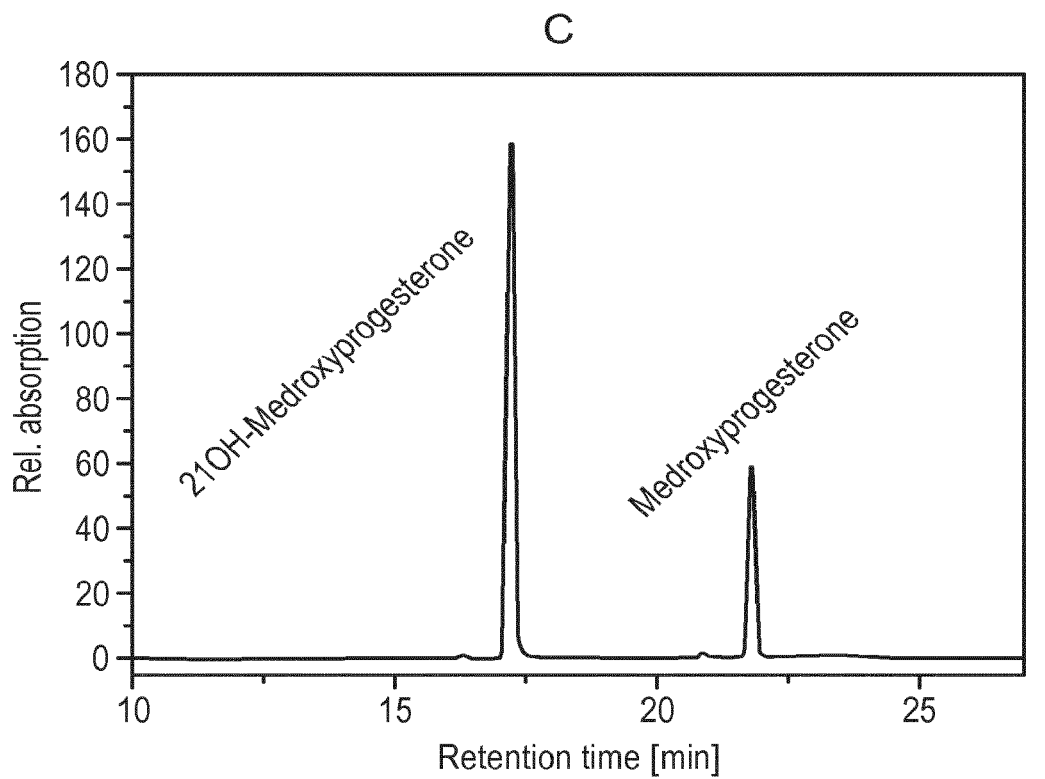
Figure 6:
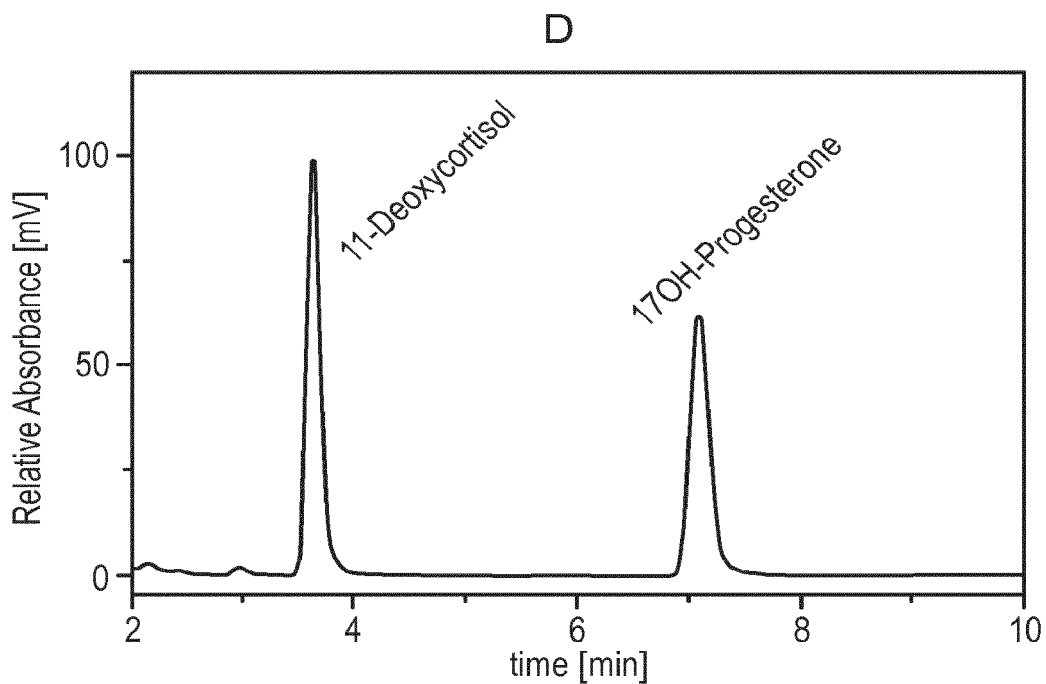
Figure 7:
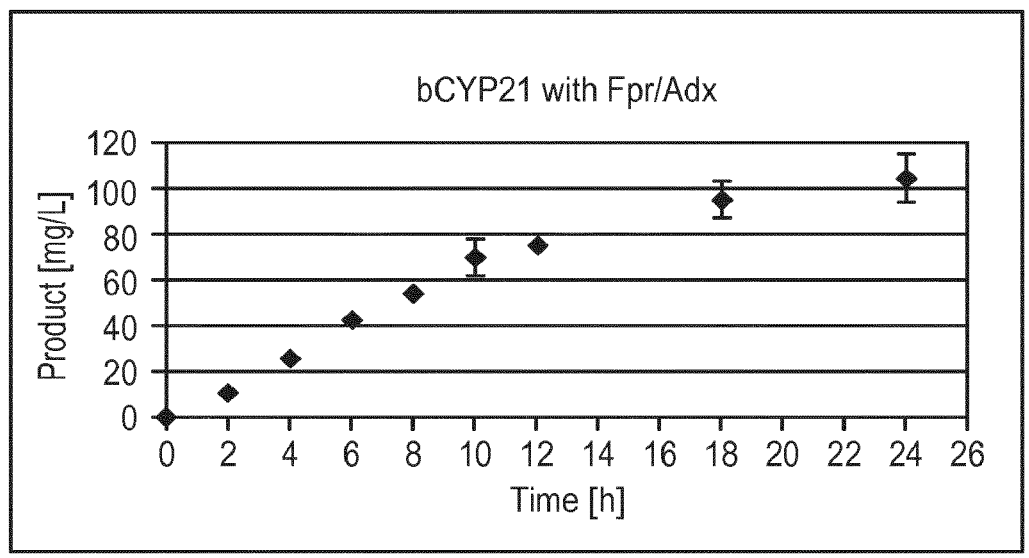
FIG. 7: Time-dependent whole cell conversion of medrane to premedrol by bovine CYP21 and described electron transfer proteins, here Fpr and Adx.

FIG. 6 shows that the steroid was converted to its 21-hydroxylated derivative and that the appearance of by-products was not observed, in contrast to a chemical synthesis. Time-dependent product formation was studied in whole cells with the six redox systems for each CYP21 isoform to determine not only an endpoint yield but also the velocity of the reaction which is of high interest regarding a biotechnological process (FIG. 7).

Next to the medrane-to-premedrol conversion, both human and bovine CYP21 were able to hydroxylate all tested 3-ketosteroids which are not yet hydroxylated at position 21. In particular, the following steroid conversions could be shown:

Medrane to premedrol (non-natural substrate)
Deltamedrane to medrol (non-natural substrate)
Progesterone to 11-deoxycorticosterone (natural substrate)
17OH-progesterone to 11-deoxycortisol (natural substrate)
Medroxyprogesterone to 21OH-medroxyprogesterone (non-natural substrate)
5α-dihydroprogesterone to 21OH-(5α-dihydroprogesterone).

The invention claimed is:

1. A process for the hydroxylation of the carbon atom 21 of a steroid, comprising the steps of:
    (a) providing a cell expressing:
        (i) a heterologous CYP21A2 protein or a functional variant thereof;
        (ii) at least one heterologous electron transfer system capable of transferring electrons to CYP21A2, wherein the at least one electron transfer system is selected from the group consisting of:
            the combination of a flavodoxin reductase (Fpr) and an adrenodoxin;
            the combination of a Fpr and the ferredoxin domain of an electron transfer domain (etp$^{fd}$);
            the combination of an adrenodoxin reductase homolog (Arh) and an adrenodoxin; and
            the combination of an Arh and etp$^{fd}$; and
        (iii) one or more chaperones facilitating folding of CYP21A2; and
    (b) adding the steroid to the cell.

2. The process of claim 1, further comprising a step (c) of extracting the 21-hydroxylated steroid from the supernatant of the cell.

3. The process of claim 1, further comprising adding one or more cell permeabilizing agents to the cell after step (b).

4. The process of claim 1, wherein the steroid is a 3-keto steroid.

5. The process of claim 4, wherein the 3-keto steroid is selected from the group consisting of medrane, deltamedrane, progesterone, 17OH-progesterone, medroxyprogesterone, and 5-α-dihydro-progesterone.

6. The process of claim 1, wherein the cell is a resting cell.

7. The process of claim 1, wherein the cell is a prokaryotic cell or a eukaryotic cell.

8. The process of claim 7, wherein the cell is an *E. coli* cell.

9. The process of claim 7, wherein the cell is a yeast cell.

10. The process of claim 1, wherein:
    (a) the Fpr is an *E. coli* Fpr;
    (b) the adrenotoxin is human or bovine Adx4-108;

(c) the Arh is *S. pombe* adrenodoxin reductase homolog (Arh1); and/or (d) etp$^{fd}$ is the ferredoxin domain of the *S. pombe* electron transfer domain (etp1$^{fd}$).

11. The process of claim 10, wherein the ferredoxin reductase is an NADPH-dependent ferredoxin reductase.

12. The process of claim 1, wherein the one or more chaperones are recombinantly expressed chaperones.

13. The process of claim 1, wherein the expression of at least one tryptophanase gene is reduced or abolished in the cell.

14. The process of claim 1, wherein the cell further expresses a heterologous gene encoding for an enzyme catalyzing a step in the heme biosynthesis pathway.

15. The process of claim 14, wherein the heterologous gene encoding for an enzyme catalyzing a step in the heme biosynthesis pathway is a hemA gene.

16. The process of claim 1, wherein the functional variant of a CYP21A2 protein has at least 20% of the ability of the unaltered CYP21A2 protein to 21-hydroxylate a steroid.

17. The process of claim 1, wherein the genes encoding for (i), (ii), and optionally (iii) are comprised in one or more expression cassettes which are integrated into the cell genome.

18. A cell expressing:
(i) a heterologous CYP21A2 protein or a functional variant thereof;
(ii) at least one heterologous electron transfer system capable of transferring electrons to CYP21A2, wherein the at least one electron transfer system is selected from the group consisting of:
the combination of a flavodoxin reductase (Fpr) and an adrenotoxin;
the combination of a Fpr and the ferredoxin domain of an electron transfer domain (etp$^{fd}$);
the combination of an adrenotoxin reductase homolog (Arh) and an adrenotoxin; and
the combination of an Arh and etp$^{fd}$; and
(iii) one or more chaperones facilitating folding of CYP21A2.

19. A multicistronic expression vector comprising:
(i) a nucleic acid encoding for a CYP21A2 protein or a functional variant thereof;
(ii) one or more nucleic acids encoding for at least one heterologous electron transfer system capable of transferring electrons to CYP21A2, wherein the at least one electron transfer system is selected from the group consisting of:
the combination of a flavodoxin reductase (Fpr) and an adrenotoxin;
the combination of a Fpr and the ferredoxin domain of an electron transfer domain (etp$^{fd}$);
the combination of an adrenotoxin reductase homolog (Arh) and an adrenotoxin; and
the combination of an Arh and etp$^{fd}$; and optionally
(iii) one or more nucleic acids encoding for chaperones facilitating folding of CYP21A2.

20. A kit comprising:
(a) the cell of claim 18;
(b) a multicistronic expression vector of claim 19; or
(c) (i) an expression vector comprising a nucleic acid encoding for a CYP21A2 protein or a functional variant thereof;
(ii) one or more expression vectors comprising one or more nucleic acids encoding for at least one heterologous electron transfer system capable of transferring electrons to CYP21A2, wherein the at least one electron transfer system is selected from the group consisting of:
the combination of a flavodoxin reductase (Fpr) and an adrenotoxin;
the combination of a Fpr and the ferredoxin domain of an electron transfer domain (etp$^{fd}$);
the combination of an adrenotoxin reductase homolog (Arh) and an adrenotoxin; and
the combination of an Arh and etp$^{fd}$; and optionally
(iii) one or more expression vectors comprising one or more nucleic acids encoding for chaperones facilitating folding of CYP21A2.

* * * * *